US00RE39005E

(19) United States
(12) Reissued Patent
Christophersen et al.

(10) Patent Number: US RE39,005 E
(45) Date of Reissued Patent: Mar. 7, 2006

(54) METHOD FOR PRODUCTION OF MALTOSE AND A LIMIT DEXTRIN, THE LIMIT DEXTRIN, AND USE OF THE LIMIT DEXTRIN

(75) Inventors: Claus Christophersen, Ringsted (DK); Sven Pedersen, Gentofte (DK); Tommy Rex Christensen, Bagsvaerd (DK)

(73) Assignee: Novozymes A/S, Bagsvaerd (DK)

(21) Appl. No.: 10/654,856

(22) PCT Filed: Oct. 13, 1994

(86) PCT No.: PCT/DK94/00383

§ 371 (c)(1),
(2), (4) Date: Apr. 9, 1996

(87) PCT Pub. No.: WO95/10627

PCT Pub. Date: Apr. 20, 1995

Related U.S. Patent Documents

Reissue of:
(64) Patent No.: 6,361,809
Issued: Mar. 26, 2002
Appl. No.: 08/628,625
Filed: Apr. 9, 1996

(30) Foreign Application Priority Data

Oct. 14, 1993 (DK) ..... 1148/93

(51) Int. Cl.
*C08B 30/00* (2006.01)

(52) U.S. Cl. ..... 426/52; 127/55; 127/69; 426/495

(58) Field of Classification Search ..... 426/38, 426/71, 52, 495; 127/38, 53, 54, 55, 69
See application file for complete search history.

(56) References Cited

U.S. PATENT DOCUMENTS 4,182,634 A * 1/1980 Yamada et al.
4,477,568 A * 10/1984 Hokse et al.
4,511,654 A * 4/1985 Rohrbach et al.
4,780,149 A * 10/1988 Kaper et al.
5,194,094 A * 3/1993 Ammeraal et al.
5,225,219 A * 7/1993 Inglett

FOREIGN PATENT DOCUMENTS

| | | | |
|---|---|---|---|
| EP | 120693 | | 10/1984 |
| EP | 0 120 693 | * | 10/1984 |
| EP | 176621 | | 4/1986 |
| EP | 0 176 621 | * | 4/1986 |
| EP | 350737 | | 1/1990 |
| EP | 0 350 737 | * | 1/1990 |
| WO | WO 91/01091 | * | 2/1991 |

OTHER PUBLICATIONS

Outtrup et al., Starch/Särke, vol. 36, No. 12, pp. 405–411 (1996).*
Verwaerde et al., Elsevier Applied Sci., pp. 117–133.*
Starch/Stärke, vol. 45, No. 9, pp. 332–325 (1993) (German).*
Verwaerde et al, Starch/Starke, vol. 45, Part 9, pp. 322–325 (1993).
H. Outtrup et al, Properties and application of a thermostable, Starch/Starke, Part 12, pp. 405–411, (1984).
F. Verwaerde et al, Product of Hydorgenated Glucose Syrups, pp. 117–135.
Hidetsugu Fuwa, Saccharification of Raw Starch, J Jpn Soc, Part 2, vol. 34, pp. 89–92, (1987) (Reference and English Translation).

* cited by examiner

*Primary Examiner*—Arthur L. Corbin
(74) *Attorney, Agent, or Firm*—Elias J. Lambiris; Jason I. Garbell

(57) ABSTRACT

In the method raw starch is treated with the amylase with the enzyme classification EC 3.21.133 below the gelatinization temperature, whereafter the maltose and the limit dextrin are recovered. The method is simple and cheap and gives rise to a maltose of high purity and to a cheap limit dextrin useable as a fat replacer in foods.

18 Claims, 2 Drawing Sheets

METHOD FOR PRODUCTION OF MALTOSE AND A LIMIT DEXTRIN, THE LIMIT DEXTRIN, AND USE OF THE LIMIT DEXTRIN

Matter enclosed in heavy brackets [ ] appears in the original patent but forms no part of this reissue specification; matter printed in italics indicates the additions made by reissue.

CROSS-REFERENCE TO RELATED APPLICATIONS

This application is a 35 U.S.C. 371 national application of PCT/DK94/00383 filed Oct. 13, 1994, which is incorporated herein by reference.

This invention is concerned with a method for production of maltose and a limit dextrin, whereby raw starch is treated with an amylase, whereafter the maltose and the limit dextrin are recovered, the limit dextrin, and a use of the limit dextrin.

BACKGROUND OF THE INVENTION

Maltose is a disaccharide, which is used in huge amounts in the candy industry. Maltose does not crystallize easily, in contradistinction to e.g. glucose, which is able to crystallize even in the presence of impurities in high concentrations. Maltose is not able to crystallize and thus to be purified further, unless the maltose used as a starting material exhibits a purity above 90%. Also, the fact that maltose does not crystallize easily is one of the reasons why maltose is a valuable raw material in the candy industry.

Maltose has also other applications, e.g. as the active component of intravenous injection liquids intended for provision of sugar for the patient and as a component in frozen deserts (due to the fact that the crystallization ability of maltose is very little), in the baking and brewing industry, and for production of maltitol, which can be used as a sweetening agent, like sorbitol, vide Glycose Sirups, Science and Technology, Elsevier Applied Science Publishers 1984, pages 117–135.

The prior art methods for production of maltose suffer from the disadvantage that they are rather cumbersome, especially if the maltose has to be prepared in a purity above 90%.

Thus, reference can be made to 44. Stärke-Tagung 21–23 April 1993 (reprint from BioTimes No. 4/93, edited by Novo Nordisk), and Die Stärke, 36 (1984), 405–411, Helle Outtrup and Barrie E. Norman. From the first of these two publications it appears that the maximum obtainable purity of maltose (when a mixture of three enzymes is used) is 80%, and from the second of these two publications it appears (page 10) that the maximum obtainable purity (at the highest enzyme dosage) is about 70%.

SUMMARY OF THE INVENTION

Thus, the purpose of the invention is the provision of a method for production of maltose, of the above indicated kind, which is simpler and cheaper in comparison to the prior art methods for production of maltose and in relation to which maltose can be obtained in a purity well above the purity obtainable according to prior art methods, i.e. a purity above 90%, and, as a spin-off effect, the provision of a new limit dextrin, and a use thereof.

The method according to the invention for production of maltose and a limit dextrin, whereby raw starch is treated with an amylase, whereafter the maltose and the limit dextrin are recovered, is characterized by the fact that the amylase is a hydrolase with the enzyme classification EC 3.2.1.133, that the temperature is lower than the lowest temperature at which the raw starch is gelatinized, and that the recovery of the maltose and the limit dextrin is performed as an ultrafiltration, whereby the maltose is in the permeate, and the limit dextrin is produced as the solid phase by liquid-solid separation of the retentate.

As indicated, the recovery of maltose is carried out as follows. After treatment of the raw starch the solid phase and the supernatant therefrom comprising mainly oligosaccharides and maltose is subjected to an untrafiltration, which yields a permeate, the dry matter of which contains more than 90% of maltose. Centrifugation or filtration of the unreacted raw starch can be carried out in a step before the ultrafiltration step, if wanted.

The gist of the invention, thus, is the recognition that a category of amylases exists, which is able to give rise to a degradation product of raw starch, which consists of a mixture of maltose and high molecular oligosaccharides, which mixture by simple ultrafiltration gives rise to a permeate with a dry matter consisting of more than 90% maltose. This is surprising because the prior art degradation products of raw starch, formed by means of amylases, comprises relatively large amounts of low molecular sugars, such as glucose and maltotriose, which would lower the purity of the maltose in the permeate far below 90%.

It goes without saying that the pH during the method should be at or in the vicinity of the pH optimum of the amylase used for the production of maltose.

EP 350737 describes a process for production of maltooligosaccharides comprising mainly maltose and maltotriose by use of raw starch as a starting material and with a specific Bacillus stearothermophilus amylase as the starch degrading enzyme. However, the classification of this Bacillus stearothermophilus amylase is not EC 3.2.1.133, and it clearly appears from the specification of EP 350737 that it is not possible to produce the maltose in a purity above 90%.

Also, according to the invention it has been found that the limit dextrin, which prima facie would be considered a waste product has applicability as a fat replacer in foods.

A preferred embodiment of the method according to the invention is characterized by the fact that the raw starch is waxy maize starch. With waxy maize starch a high yield is obtained, and also, the reaction proceeds smoothly, due to the fact that the viscosity of the reaction mixture is low.

A preferred embodiment of the method according to the invention is characterized by the fact that the hydrolase with the enzyme classification EC 3.2.1.133 is a B. stearothermophilus amylase with a molecular weight of 70,000±5,000. Reference is made to the paper "Properties and application of a thermostable, maltogenic amylase, produced by a strain of Bacillus modified by recombinant-DNA techniques" by Helle Outtrup and Barrie E. Norman of Novo Nordisk A/S, Die Stärke, 36 (1984), 405–411, in which this amylase is described. In this paper the prior art amylase is used exclusively in connection with liquefied starch as a starting material, and it has not been possible to prepare a final product with a purity above 90% by means of this prior art method.

A preferred embodiment of the method according to the invention is characterized by the fact that the ultrafiltration is carried out simultaneously with the treatment of the raw starch with the amylase, and that the temperature is above 40° C. In this manner the process time can be reduced, and also, the yield of the maltose in the permeate is improved.

Also, the invention comprises the limit dextrin, prepared as in the method according to the invention. If for some reason, the limit dextrin in a specific context is the important product, and the maltose is of no significance, the ultrafiltration is unnecessary, as the limit dextrin can be produced directly after the amylolytic degradation by solid-liquid separation of the amylolytic degradation mixture and by washing of the solid phase. Besides being characterized by the fact that it is produced by means of the method according to the invention the limit dextrin according to the invention is characterized by the fact that the ratio α-1,4 bonds/α-1,6 bond s is smaller than for the raw starch (which is consistent with the assumption that the special amylase only cleaves the α-1,4 bonds of the starch), that the DE is 6.3 for waxy maize starch and 7.9 for common corn starch, and that the molecular weight distribution is similar to the molecular weight distribution of the native, raw starch, but with a somewhat lower average value. The above indicated characterization by means of the ratio α-1,4 bonds/α-1,6 bonds can be quantified as follows: this ratio is 9 for the limit dextrin derived from the waxy maize starch and 20 for the genuine waxy maize starch, and it is 13 for the limit dextrin derived from the common corn starch and 50 for the genuine common corn starch. Due to the fact that the limit dextrin according to the invention prima facie would be considered a waste product, it is very cheap.

Finally, the invention comprises the use of the limit dextrin according to the invention as a fat replacer in foods. Surprisingly it has been found that this very cheap limit dextrin can be used as a fat replacer, which exhibits the same good organoleptic properties as traditional fat replacers. Also, the limit dextrin according to the invention can be used in confections with a gum structure, in soft drinks, in viscous dairy products, and as a carrier for dried liquids.

The invention will be illustrated in the following examples. In the examples the content of dry substance (DS) in the starch slurry is 25% (Example 1) and 20% (Example 2). The DS content in relation to this invention advantageously can have a value between 10% and 50%, preferably between 20% and 40%.

EXAMPLE 1

Figure 1:
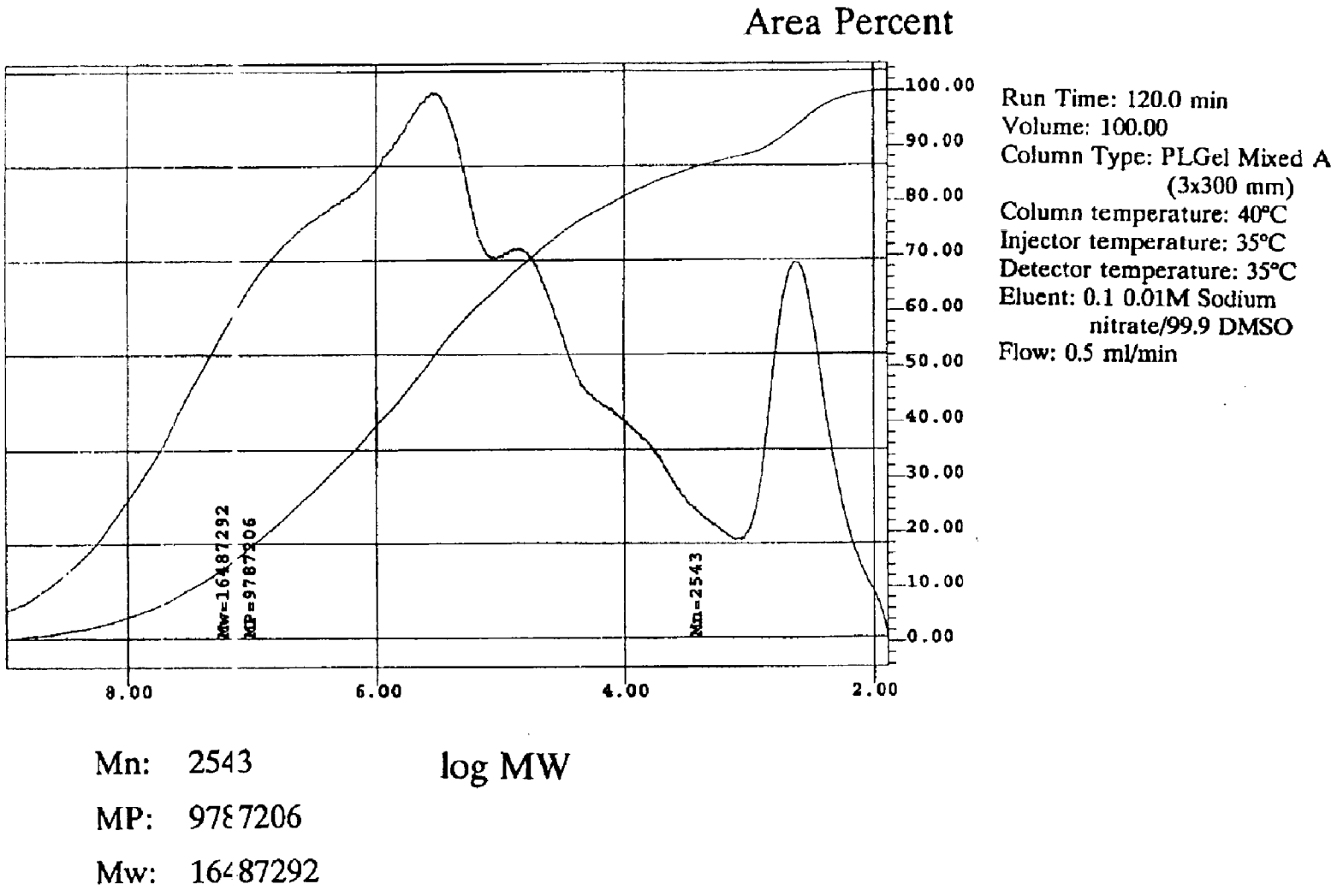
FIG. 1 is the determination of molecular weight distribution of the samples described in Example 1 calculated from a calibration curve based on pullalan standards.

1388 g of waxy maize starch (American Maize Co.) (90% DS=1250 g) was suspended in 3612 g deionized water to make a 25% DS slurry. pH was adjusted to 5.1. 8.33 g of Maltogenase (EC 3.2.1.133, glucan 1,4-α-maltohydrolase, Novo Nordisk N/S) having an activity of 1500 MANU/g was added to the slurry. The definition of the enzyme activity unit MANU appears from AF 203/1, which is obtainable on request from Novo Nordisk A/S, Novo Allé, DK-2880 Bagsvaerd, Denmark. As a substrate in relation to the activity determination, carried out at pH 5 and at 37° C., is used maltotriose, which is degraded to glucose or maltose, which again is determined spectrophotometrically.

The slurry was incubated in a water bath at 60° C. for 46 hours. The reactor was coupled to an ultrafiltration module (pump: Eagholm, type BF 471M44; module: Mini-Lab 10, DDS RO-Division, Denmark; UF membranes: Dow Danmark, Type GR90PP, cut off 2000; filtration area: 0.0336 $m^2$), and during the incubation, the reaction mixture was pumped through the membrane module with a flow of 440 l/hour giving rise to a retentate and a permeate. During the reaction time 3120 ml of permeate was collected giving a permeate flux of 2000 ml/hour/$m^2$. The initial inlet pressure was 2.1 bar and due to increase of concentration and viscosity of the reaction 2200 ml of deionized water was added from time to time in order to keep the DS content in the reaction mixture at a reasonable level (about 25% DS). At the end of the reaction pH had increased to 6.1 in the reaction mixture.

The DS content in the permeate was 11.0% and the density was 1.04 g/ml giving a yield of 357 g maltose corresponding to 28%. The product consisted of 94% maltose, 3.5% glucose, and 2.5% of higher oligosaccharides (determined by HPLC).

40.5 g of the above indicated retentate was centrifuged at 4,000 rpm for 40 minutes. The precipitate and the supernatant from the centrifugation were separated and the precipitate was washed 4 times with deionized water. The washed precipitate was dried in an oven at 50° C. over night. 0.294 g of precipitate was isolated corresponding to a yield of 5.9% of limit dextrin.

The precipitate was characterized by NMR (Nuclear Magnetic Resonance) spectroscopy and GPC (Gel Permeation Chromatography). For the NMR experiment 15 mg of the precipitate was dissolved in 0.5 ml DMSO-$d_6$ (DMSO is an abbreviation for Dimethyl Sulfoxide, and $d_6$ signifies that 6 denterium atoms are present in the DMSO molecure instead of 6 hydrogen atoms) by heating to about 50° C. for about ½ hour. The NMR experiments were perfromed at 60° C. using a Bruker AC 300 spectrometer. The α-1,4/α-1,6 ratio was determined by integration of signals from the α-1,4 linkages (5.2 ppm), the α-ends (5.1 ppm), the α-1,6 linkages (4.65 ppm) and the β-ends (4.35 ppm).

For the GPC experiment 10 mg of the precipitate was dissolved in 4 ml DMSO. The samples were analyzed on three PLGel 20 μm MIXED A (300×7.5 mm) columns (from Polymer Laboratories, England) in series using Waters HPLC (High Performance Liquid Chromatography) equipment.

The molecular weight distribution of the samples was calculated from a calibration curve based on pullulan standards, vide FIG. 1. On FIG. 1 the curve with the peaks is the true molecular weight distribution curve, whereas the constantly increasing curve is the accumulated molecular weight distribution curve, Mn is the mean molecular weight according to number, Mw is the mean molecular weight according to weight, and MP is the molecular weight corresponding to the highest peak of the true molecular weight distribution curve.

EXAMPLE 2

1152 g of common corn starch (with a % DS of 86.8, i.e. corresponding to 1000 g of dry starch) was suspended in 4000 g deionized water to make a 20% DS slurry. pH was adjusted to 5.1. 6.66 g of Maltogenase (EC 3.2.1.133, glucan 1,4-α-maftohydrolase, Novo Nordisk A/S) having an activity of 1500 MANU/g was added to the slurry.

The slurry was incubated in a water bath at 60° C. for 46 hours. The reactor was coupled to an ultrafiltration module (pump: Eagholm, type BF 471M44; module: Mini-Lab 10, DDS RO-Division, Denmark; UF membranes: Dow Danmark, Type GR90PP, cut off 2000; filtration area: 0.0336 $m^2$), and during the incubation, the reaction mixture was pumped through the membrane module with a flow of 540 l/hour giving rise to a retentate and a permeate. During the reaction time 1845 ml of permeate was collected giving a permeate flux of 1194 ml/hour/$m^2$. The initial inlet pressure was 1.8 bar, and due to increase of concentration and viscosity of the reaction mixture, the inlet pressure at the end of the reaction was 3.4. bar. During the reaction about 1000 ml of deionized water was added from time to time in order to keep the DS content in the reaction mixture at about 20% DS. At the end of the reaction the DS content in the reaction mixture was 23.5%.

The DS content in the permeate was 9.35%, and the density was 1.04 g/ml giving a yield of 178.7 g of maltose corresponding to 17.8%. The product consists of 94% of maltose, 3.7% of glucose and 2.3% of higher oligosaccharides (determined by HPLC).

41.0 g of the above indicated retentate was centrifuged at 4,000 rpm for 40 minutes. The precipitate and the supernatant were separated and the precipitate was washed 4 times with deionized water. The washed precipitate was dried in an oven at 50° C. over night. 0.826 g of precipitate was isolated corresponding to a yield of 10.0% of limit dextrin.

The precipitate was characterized by NMR spectroscopy and GPC. For the NMR experiment 15 mg of the precipitate was dissolved in 0.5 ml DMSO-$d_6$ by heating to about 50° C. for about ½ hour. The NMR experiments were performed at 60° C. using a Bruker AC 300 spectrometer. The α-1,4/α-1,6 ratio was determined by integration of signals from the α-1,4 linkages (5.2 ppm), the α-ends (5.1 ppm), the α-1,6 linkages (4.65 ppm) and the β-ends (4.35 ppm).

For the GPC experiment 10 mg of the precipitate was dissolved in 4 ml of DMSO. The samples were analyzed on three PLGel 20 μm MIXED A (300×7.5 mm) columns in series using Waters HPLC equipment.

Figure 2:
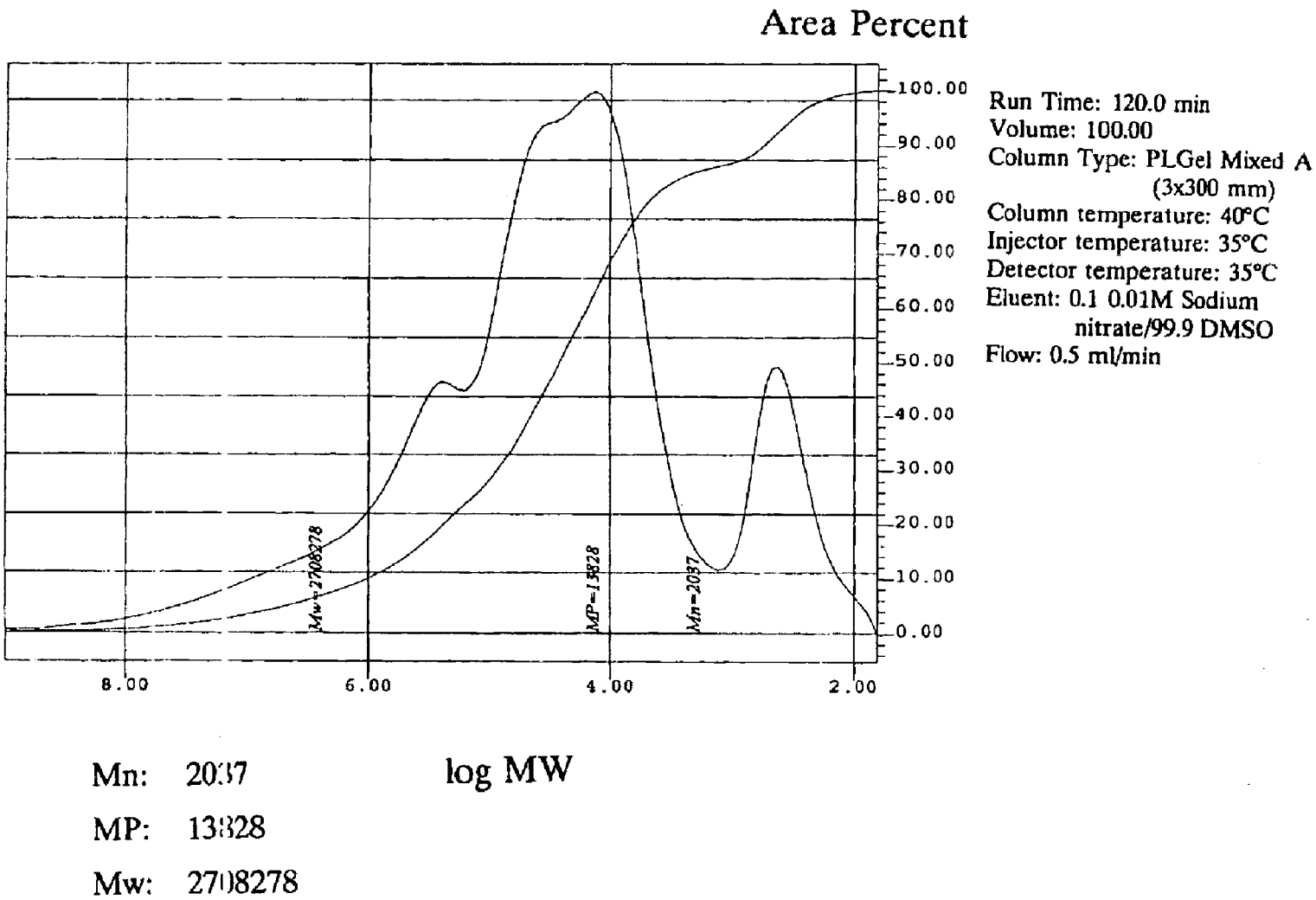
FIG. 2 is the determination of molecular weight distribution of the samples described in Example 2 calculated as described above.

The molecular weight distribution of the samples was calculated from a calibration curve based on pullulan standards, vide FIG. 2. On FIG. 2 the curve with the peaks is the true molecular weight distribution curve, whereas the constantly increasing curve is the accumulated molecular weight distribution curve, Mn is the mean molecular weight according to number, Mw is the mean molecular weight according to weight, and MP is the molecular weight corresponding to the highest peak of the true molecular weight distribution curve.

In relation to examples 1 and 2 it can be noted that the maltose yield will be larger, if the ultrafiltration is carried out for a longer time, the purity of the maltose being kept at the same high level as indicated.

What is claimed is:

1. A method for producing maltose and a limit dextrin, comprising:

(a) treating a raw starch with a hydrolase classified as EC 3.2.1.133, wherein said treatment of the starch is performed at a temperature above 40° C., and below the lowest temperature at which the raw starch is gelatinized;

(b) subjecting the treated starch to ultrafiltration to form a permeate comprising the maltose, and a retentate comprising the limit dextrin, wherein the maltose content of the permeate is more than 90%; and (c) recovering the maltose from the permeate and the limit dextrin from the retentate by subjecting the retentate to liquid-solid separation.

2. The method according to claim 1, wherein the raw starch is waxy maize starch.

3. The method according to claim 1, wherein the hydrolase is a B. stearothermophilus amylase with a molecular weight of 70,000±5,000.

4. The method according to claim 1, wherein the ultrafiltration is carried out simultaneously with the treatment of the raw starch with the [amylase] *hydrolase*.

*5. The method according to claim 1, wherein the raw starch is corn starch.*

*6. A method for producing a degradation product of raw starch, comprising*

*treating raw starch with a hydrolase classified as EC 3.2.1.133, wherein said treatment of the raw starch is performed at a temperature above 40° C. and below the lowest temperature at which the raw starch is gelatinized.*

*7. The method according to claim 6, wherein the raw starch is waxy maize starch.*

*8. The method according to claim 6, wherein the hydrolase is a B. stearothermophilus amylase with a molecular weight of 70,000±5,000.*

*9. The method according to claim 6, wherein the raw starch is corn starch.*

*10. A method for producing maltose, comprising:*

*(a) treating a raw starch with a hydrolase classified as EC 3.2.1.133, wherein said treatment of the starch is performed at a temperature above 40° C., and below the lowest temperature at which the raw starch is gelatinized;*

*(b) subjecting the treated starch to ultrafiltration to form a permeate comprising the maltose, and*

*(c) recovering the maltose from the permeate.*

*11. The method according to claim 10, wherein the raw starch is waxy maize starch.*

*12. The method according to claim 10, wherein the hydrolase is a B. stearothermophilus amylase with a molecular weight of 70,000±5,000.*

*13. The method according to claim 10, wherein the ultrafiltration is carried out simultaneously with the treatment of the raw starch with the hydrolase.*

*14. The method according to claim 10, wherein the raw starch is corn starch.*

*15. A method for producing a limit dextrin, comprising:*

*(a) treating a raw starch with a hydrolase classified as EC 3.2.1.133, wherein said treatment of the starch is performed at a temperature above 40° C., and below the lowest temperature at which the raw starch is gelatinized; and*

*(b) recovering the limit dextrin from the treated raw starch.*

*16. The method according to claim 15, wherein the raw starch is waxy maize starch.*

*17. The method according to claim 15, wherein the hydrolase is a B. stearothermophilus amylase with a molecular weight of 70,000±5,000.*

*18. The method according to claim 15, wherein the raw starch is corn starch.*

* * * * *